US006934023B2

(12) United States Patent
Kawamura

(10) Patent No.: US 6,934,023 B2
(45) Date of Patent: Aug. 23, 2005

(54) METHOD OF POLARIMETRY

(75) Inventor: Tatsurou Kawamura, Kyotanabe (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 405 days.

(21) Appl. No.: 09/982,159

(22) Filed: Oct. 19, 2001

(65) Prior Publication Data
US 2002/0075480 A1 Jun. 20, 2002

(30) Foreign Application Priority Data
Oct. 24, 2000 (JP) .................................. 2000-323885

(51) Int. Cl.$^7$ ................................................. G01J 4/00
(52) U.S. Cl. .................... 356/364; 356/368; 356/369
(58) Field of Search ................................ 356/364, 367, 356/368, 369

(56) References Cited

U.S. PATENT DOCUMENTS

| 3,312,141 | A | | 4/1967 | Cary |
| 4,988,199 | A | * | 1/1991 | Paul ........................... 356/368 |
| 6,036,922 | A | | 3/2000 | Kawamura et al. |
| 6,046,804 | A | | 4/2000 | Kawamura et al. |
| 6,137,933 | A | | 10/2000 | Hunter et al. |
| 6,166,807 | A | | 12/2000 | Kawamura et al. |
| 6,269,203 | B1 | | 7/2001 | Davies et al. |
| 6,297,057 | B1 | | 10/2001 | Kawamura et al. |
| 6,620,622 | B1 | * | 9/2003 | Kawamura ................... 436/164 |

FOREIGN PATENT DOCUMENTS

| EP | 0 805 352 | 11/1997 |
| EP | 1 065 497 | 1/2001 |
| JP | 63-012984 | 1/1988 |
| JP | 6-102175 | 4/1994 |
| JP | 6-324047 | 11/1994 |
| JP | 09-145605 | 6/1997 |
| JP | 2000-046730 A | 2/2000 |
| WO | WO 02/067475 A2 | 8/2002 |

OTHER PUBLICATIONS

"Numerical Recipes in C" 1992, Cambridge University Press, Chapter 15, Modeling of Data, second edition, pp. 656–666.

Churin et al., "Passband flattening and broadening techniques for high spectral efficiency wavelength demultiplexers", Electronic Letters, Jan. 7, 1999, vol. 35, No. 1.

International Search Report for PCT/EP02/09295.

* cited by examiner

Primary Examiner—Gregory J. Toatley, Jr.
Assistant Examiner—Roy M. Punnoose
(74) Attorney, Agent, or Firm—McDermott Will & Emery LLP

(57) ABSTRACT

In order to obtain a simple and highly reliable method of polarimetry, there is provided a method of polarimetry characterized by calculating an angle of rotation from discrete 2 or 3 measuring points, and performing again the measurement on the measuring point which is not effective.

32 Claims, 7 Drawing Sheets

F I G. 3
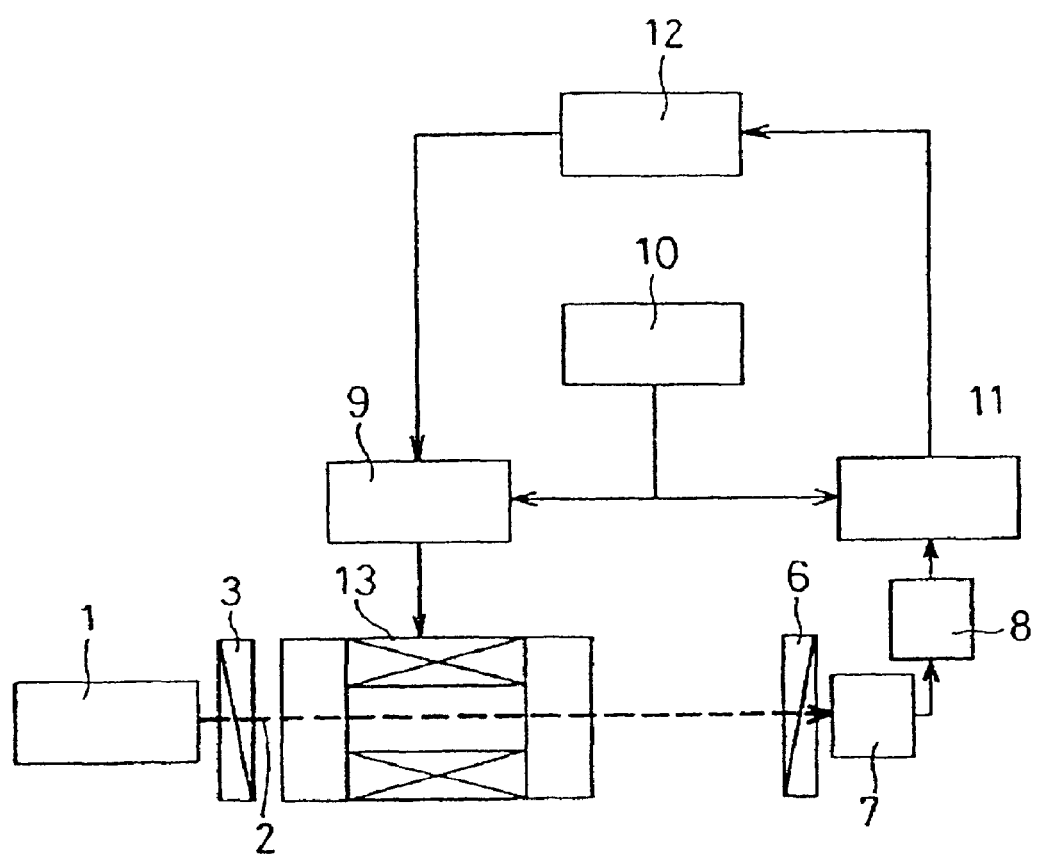

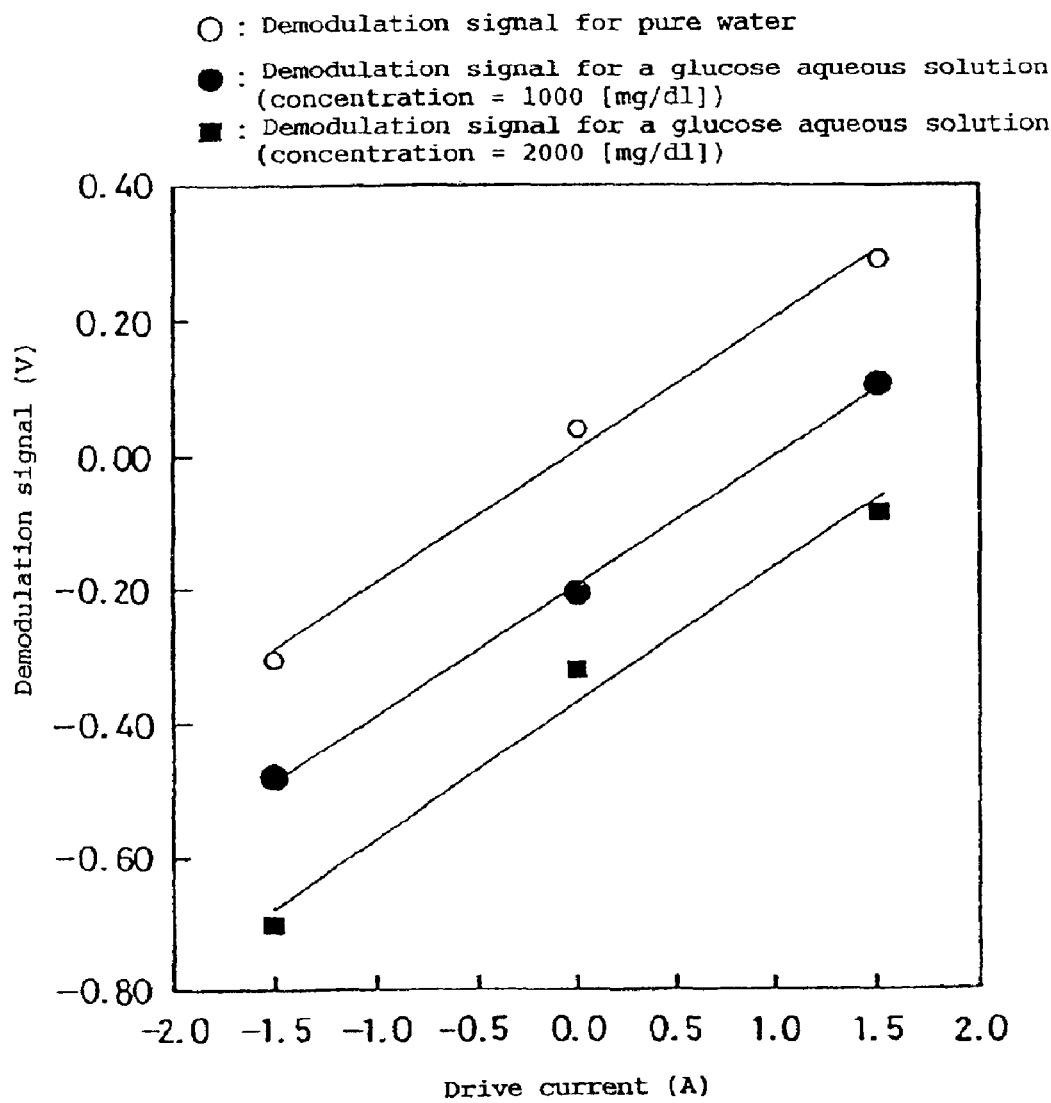
F I G. 4

METHOD OF POLARIMETRY

BACKGROUND OF THE INVENTION

The present invention relates to a method of polarimetry for use in an identification, examination on the purity, determination of the concentration, and the like of a solute in a sample solution.

A polarimeter is employed as an optical rotation detecting type saccharimeter for detecting the concentrations of fructose, sucrose, glucose, and the like contained in an aqueous solution. Such a polarimeter can also determine especially the concentrations of spontaneously optical active substances such as glucose and protein in a urine and, therefore, is expected to come into wide use as a urinalysis equipment which requires no consumable items such as test papers.

FIG. 7 shows a conceptual constitution of one example of conventional polarimeters. The polarimeter is for determining the magnitude of spontaneously optical rotatory power, i.e., an angle of rotation attributed to a spontaneously optical rotatory power of a spontaneously optical active substance in a sample. In concrete, the angle of spontaneously optical rotation is determined on the basis of an angle of magneto-rotation (so called compensated value) by an optical Faraday effect when the spontaneously optical rotation attributed to the spontaneously optical active substance is canceled (compensated) by the magneto-rotation.

In the polarimeter, a light source 14 for projecting a substantially parallel light, configured with a sodium lamp, a band-pass filter, a lens, a slit and the like, projects a substantially parallel light composed of, for example, a sodium D ray having a wavelength of 589 nm. A polarizer 15 transmits only a component that has a specific plane of vibration out of the incident light projected from the light source 14.

A sample cell 16 for holding a sample has a pair of mutually opposing transparent transmission surfaces, and is arranged so that the light projected from the light source 14 can transmit through the inside thereof. An analyzer 17 transmits only a component that has another specific plane of vibration out of the light transmitted through the sample cell 16. The relative angle Θ formed between the transmission axis of the polarizer 15 and the transmission axis of the analyzer 17 is fixed at π/2.

A photosensor 18 detects the component transmitted through the analyzer 17 out of the light projected from the light source 14. A Faraday cell 19 functions as an optical modulator for modulating and controlling the plane of vibration of the light projected from the light source 14 on the basis of a modulation signal outputted from a signal generator 23 and a control signal outputted from a computer 22. The Faraday cell 19 is driven by a Faraday cell driver 20.

Further, a lock-in amplifier 21 performs a phase sensitive detection on the output signal from the photosensor 18 by using the modulation signal outputted from the signal generator 23 as a reference signal. The computer 22 calculates the angle of rotation attributed to the sample accommodated in the sample cell 16 on the basis of the control signal, and the output signal from the lock-in amplifier 21.

As described above, by sweeping the angle of the plane of vibration by the Faraday cell, it becomes possible to achieve simplification and compactness thereof as compared with apparatuses using other means for modulating the plane of vibration.

The principle of the conventional polarimeter will be described in the followings.

In first, the polarization direction is modulated with an amplitude="δ" and an angular frequency of "ω" in the Faraday cell 19. In this step, the intensity "I" of the light that reaches the photosensor 18 is represented by the following equation (6):

$$I = T \times I_0 \times (COS(\Theta - \alpha + \beta + \delta \times SIN(\omega \times t)))^2 \qquad (6)$$

where "T" denotes a transmittance of the sample, "$I_0$" denotes an intensity of the light incident upon the sample, "Θ" denotes a relative angle formed between the optical axes of the polarizer 15 and the analyzer 17, "α" denotes an angle of rotation attributed to the sample, "β" denotes an angle of rotation due to the Faraday cell 19, and "t" denotes the time). It is noted that their respective transmission and reference losses of the sample cell and the analyzer are ignored.

In the equation (6), Θ is fixed to be π/2, and hence the following equation (7) is given:

$$I = T \times I_0 \times (SIN(\beta - \alpha + \delta \times SIN(\omega \times t)))^2 \qquad (7)$$

Herein, in case of β−α=0, in other words, when the angle of rotation of the polarization direction due to the optical rotation is compensated by the angle of rotation due to the Faraday cell 19, the equation (7) is expressed as the following equation (8):

$$\begin{aligned} I &= (\tfrac{1}{2}) \times T \times I_0 \times (1 - \cos(2 \times \delta \times SIN(\omega \times t))) \\ &\quad (\tfrac{1}{2}) \times T \times I_0 \times (1 - (J_0(2 \times \delta) \\ &\quad + 2 \times J_2(2 \times \delta) \times COS(2 \times \omega \times t) \\ &\quad + \ldots)) \end{aligned} \qquad (8)$$

where Jn(x) is an nth-degree Bessel function).

The equation (8) indicates that "I" does not contain the modulation frequency component "ω" in this case. Approximately considering this, i.e., assuming that the angle of rotation attributed to the sample and the amplitude of the modulation are small, |β−α|<<1, and δ<<1, the equation (7) is approximated to the following equation (9).

$$\begin{aligned} I &\approx T \times I_0 \times (\beta - \alpha + \delta \times SIN(\omega \times t))^2 \\ &= T \times I_0 \times ((\beta - \alpha)^2 + 2 \times (\beta - \alpha) \times \delta \times SIN(\omega \times t) + \\ &\quad (\delta \times SIN(\omega \times t))^2) \\ &= T \times I_0 \times ((\beta - \alpha)^2 + 2 \times (\beta - \alpha) \times \delta \times SIN(\omega \times t) + \\ &\quad (\delta^2 / 2 \times (1 - COS(2 \times \omega \times t)))) \end{aligned} \qquad (9)$$

This indicates that respective signal components with angular frequencies of 0 (DC), "ω" and "2×ω" are present in the output signal "I" from the photosensor. By the phase sensitive detection of the signal "I" using the modulation signal as a reference signal in the lock-in amplifier, it is possible to pick up the component of the angular frequency "ω", i.e., the signal "S" shown by the following equation (10):

$$S = T \times I_0 \times 2 \times (\beta - \alpha) \times \delta \qquad (10)$$

This signal "S" equals to zero only in case of β=α, and the signal "S" equal to zero denotes the extinction point. A polarized light is rotated, in other words, "β" is controlled by the Faraday cell 19 to obtain "β" when "S" becomes zero.

The resulting value of "β" is the angle "α" of rotation. The same is also true for the case where this process is considered on the basis of the equation (8). The output signal becomes zero upon the phase sensitive detection of the value "I" in case of β=α. Therefore, "β" is controlled so that "S" becomes zero. Then, the angle "α" of rotation is determined from the value of "β" at this step.

As described above, by modulating the angle of plane of vibration of light, it is possible to pick up only the signal "S" of the modulated frequency component selectively while separating the signal from noises attributed to an intensity of the light source, a fluctuation and radiation of the power source, and the like, thereby deriving a signal with a high S/N ratio. Therefore, the extinction point can be determined accurately by using this value of the signal "S", and hence the angle "α" of rotation can be determined with high precision. Simultaneously, control of the polarization direction eliminates the necessity of a large scale mechanical mechanism.

On the other hand, as a conventional examination method for examining glucose, protein and the like in a urine, there is a method in which a test paper or the like containing a reagent is dipped in a urine, and the color reaction thereof is observed by means of a spectroscope or the like. This method requires the use of a consumable article such as a test paper. However, if the angle of rotation attributed to the urine is measured by means of the high precision polarimeter described above, it is possible to detect the angles of rotation attributed to optical active substances present in the urine at a low concentration such as glucose and protein. Consequently, it is possible to calculate the concentrations thereof on the basis of the detected values. As a result of this, it becomes possible to examine the glucose and protein concentrations in a urine without any consumable article.

However, in the above-described method, if there occur microparticles such as bubbles and dust in the optical path for the substantially parallel light in the sample cell when "β" is controlled so that "S" becomes zero, the feedback loop is not stabilized. Accordingly, additional time may be taken to obtain the measurement result, and hence the duration of the measurement time is not stabilized.

Further, a feedback loop is preferably constructed to control "β" so that "S" becomes zero. For this reason, "β" is desirably changed continuously.

In view of the foregoing problems in the prior art, it is therefore an object of the present invention to provide a method of polarimetry which is less susceptible to the influences of microparticles such as bubbles and dust, provides a constant measurement time, and has high reliability.

BRIEF SUMMARY OF THE INVENTION

The present invention relates to a method of polarimetry by allowing a light with a known polarization direction "X" to be incident upon a sample, detecting a polarization direction of a light transmitted through the sample, and measuring an angle of rotation of a polarization direction in the sample on the basis of the difference between the polarization directions of the incident light and the transmitted light, the method comprising the steps of:

changing and modulating the polarization direction "X" of the incident light;

detecting only a polarized component in a specific direction out of the light transmitted through the sample by a photosensor to obtain an output signal;

performing a phase sensitive detection on the output signal by using a signal for the modulating as a reference signal to obtain a demodulation signal "Y";

calculating an angle of rotation from 3 or more measuring points "Pi" (Xi, Yi) obtained from 3 or more polarization signals "Xi", where i denotes an integer of from 1 to n, where n denotes 3 or more, discretely selected from the polarization direction "X", and 3 or more demodulation signals "Yi", where i denotes an integer of from 1 to n and n denotes 3 or more, respectively corresponding to the polarization signals Xi; and measuring repeatedly at least one measuring point "Pi" out of the 3 or more measuring points "Pi" (Xi, Yi) when the calculated angle of rotation is judged not effective, to calculate again the angle of rotation on the basis of the measuring point "Pi" (Xi, Yi) measured repeatedly, and repeating the measurement until the angle of rotation is judged effective.

In the above-mentioned method of polarimetry, it is effective that when the number of the repeated measurement exceeds a prescribed number, the measurement action is stopped to stop the polarimetry for the sample.

It is preferable that at least one measuring point "Pj" (Xj, Yj), where Xj≠Xi, other than the 3 or more measuring points "Pi" (Xi, Yi) is measured in the repeated measurement.

It is preferable that the polarization direction "X" of the incident light is discretely changed into 3 or more polarization signals "Xi".

It is preferable that the 3 or more measuring points "Pi" (Xi, Yi) are subjected to a linear regression treatment by using the "Xi" as criterion variables and the "Yi" as dependent variables on the basis of the principle of a least squares method to calculate a regression line represented by the equation (1):

$$Y = A + B \times X \tag{1}$$

where "Y" denotes a variable indicating the demodulation signal, "A" denotes a constant calculated, "B" denotes another constant calculated, and "X" denotes a variable indicating the polarization direction, and "X" is calculated from "A", "B" and a prescribed "Y" of the regression line to calculate the angle of rotation attributed to the sample on the basis of the "X".

It is preferable that the calculated angle of rotation is judged effective when the "B" is not less than a prescribed minimum value or not more than a prescribed maximum value.

It is preferable that the prescribed maximum value of the "B" is one calculated when a sample having a maximum transmittance is measured out of samples to be measured.

It is preferable that the reliability of the calculated angle of rotation is evaluated on the basis of the fit between the measuring points "Pi" and the regression line.

It is preferable that the fit between the measuring points "Pi" and the regression line is judged by using the sum "C" of squares of deviation represented by the following equation (2):

$$C = \Sigma (\delta i)^2 \tag{2}$$

where $\delta i = Y i - A - B \times X i$, i denotes an integer of 1 to n, where n is 3 or more, Σ denotes the total sum when the values of "i" are from 1 to n, "D" represented by the following equation (3):

$$D = C / \Sigma (A + B \times X i)^2 \tag{3}$$

or, the correlation coefficient "R" represented by the following equation (4):

$$R = \frac{\left\{\sum (Xi-x) \times (Yi-y)\right\}/}{\left\{\sum (Xi-x)^2 \times \sum (Yi-y)^2\right\}^{1/2}} \quad (4)$$

where x=(ΣXi)/n, y=(ΣYi)/n, as an index.

It is preferable that the calculated angle of rotation is judged effective when the index is not more than a prescribed maximum value and/or not less than a prescribed minimum value. In concrete, it is preferable that the calculated angle of rotation is judged effective when the "C" and/or the "D" is not more than a prescribed maximum value and/or when the "R" is not less than a prescribed minimum value.

Further, the present invention also relates to a method of polarimetry by applying a magnetic field to a sample containing a spontaneously optical active substance and a magneto-optical active substance, allowing a light with a known polarization direction "X" to be incident upon the sample, changing and modulating a polarization direction of a light transmitted through the sample, and calculating an angle of rotation attributed to the sample on the basis of a magnitude of the magnetic field when an amount of change in an angle of rotation attributed to the spontaneously optical active substance and an amount of change in an angle of rotation attributed to the magnetic field satisfy a prescribed relation, the method comprising the steps of:

changing and modulating the polarization direction "X" of the incident light by applying the magnetic field;

detecting only a polarized component in a specific direction out of the light transmitted through the sample by a photosensor to obtain an output signal;

performing a phase sensitive detection on the output signal by using a signal for the modulating as a reference signal to obtain a demodulation signal "Y";

calculating an angle of rotation from 3 or more measuring points "Pi" (Xi, Yi) obtained from the magnetic field strengths "Xi", where i denotes an integer of from 1 to n and n denotes 3 or more, corresponding to 3 or more polarization signals discretely selected from the polarization direction "X", and 3 or more demodulation signals "Yi", where i denotes an integer of from 1 to n and n denotes 3 or more, respectively corresponding to the magnetic field strengths "Xi"; and measuring repeatedly at least one measuring point "Pi" out of the 3 or more measuring points "Pi" (Xi, Yi) when the calculated angle of rotation is judged not effective, to calculate again the angle of rotation on the basis of the measuring point "Pi" (Xi, Yi) measured repeatedly, and repeating the measurement until the angle of rotation is judged effective.

It is preferable that when the number of the repeated measurement exceeds a prescribed number, the measurement action is stopped to stop the paolarimetry for the sample.

It is preferable that at least one measuring point "Pj" (Xj, Yj), where Xj≠Xi, other than the 3 or more measuring points "Pi" (Xi, Yi) is measured in the repeated measurement.

It is preferable that the magnetic field strength is discretely changed into 3 or more magnetic field strengths.

It is preferable that the 3 or more measuring points "Pi" (Xi, Yi) are subjected to a linear regression treatment by using the "Xi" as criterion variables and the "Yi" as dependent variables on the basis of the principle of a least squares method to calculate a regression line represented by the equation (1):

$$Y = A + B \times X \quad (1)$$

where "Y" denotes a variable indicating the demodulation signal, "A" denotes a constant calculated, "B" denotes another constant calculated, and "X" denotes a variable indicating the polarization direction, and "X" is calculated from "A", "B" and a prescribed "Y" of the regression line to calculate the angle of rotation attributed to the sample on the basis of the "X".

It is preferable that the calculated angle of rotation is judged effective when the "B" is not less than a prescribed minimum value or not more than a prescribed maximum value.

It is preferable that the prescribed maximum value of the "B" is one calculated when a sample having a maximum transmittance is measured out of samples to be measured.

It is preferable that the reliability of the calculated angle of rotation is evaluated on the basis of the fit between the measuring points "Pi" and the regression line.

It is preferable that the fit between the measuring points "Pi" and the regression line is judged by using the sum "C" of squares of deviation represented by the following equation (2):

$$C = \Sigma(\delta i)^2 \quad (2)$$

where δi=Yi−A−B×Xi, i denotes an integer of 1 to n, where n is 3 or more, Σ denotes the total sum when the values of "i" are from n to 1, "D" represented by the following equation (3):

$$D = C/\Sigma(A + B \times Xi)^2 \quad (3)$$

or, the correlation coefficient "R" represented by the following equation (4):

$$R = \frac{\left\{\sum (Xi-x) \times (Yi-y)\right\}/}{\left\{\sum (Xi-x)^2 \times \sum (Yi-y)^2\right\}^{1/2}} \quad (4)$$

(where x=(ΣXi)/n, y=(ΣYi)/n) as an index.

It is preferable that the calculated angle of rotation is judged effective when the index is not more than a prescribed maximum value and/or not less than a prescribed minimum value. In concrete, it is preferable that the calculated angle of rotation is judged effective when the "C" and/or the "D" is not more than a prescribed maximum value and/or when the "R" is not less than a prescribed minimum value.

Then, the present invention relates to a method of polarimetry by allowing a light with a known polarization direction "X" to be incident upon a sample, detecting a polarization direction of a light transmitted through the sample, and measuring an angle of rotation of a polarization direction in the sample on the basis of the difference between the polarization directions of the incident light and the transmitted light, the method comprising the steps of:

changing and modulating the polarization direction "X" of the incident light;

detecting only a polarized component in a specific direction out of the light transmitted through the sample by a photosensor to obtain an output signal;

performing a phase sensitive detection on the output signal by using a signal for said modulating as a reference signal to obtain a demodulation signal "Y"; and calculating an angle of rotation from two measuring points "Pi" (Xi, Yi) obtained from two polarization signals "Xi", where i denotes 1 and 2, discretely selected from the polarization direction "X", and two demodulation signals "Yi", where i denotes 1 and 2, respectively corresponding to the polarization signals Xi.

It is preferable that at least one measuring point "Pi" out of the two measuring points "Pi" (Xi, Yi) is measured repeatedly when the calculated angle of rotation is judged not effective, to calculate again the angle of rotation on the basis of the measuring point "Pi" (Xi, Yi) measured repeatedly, and the measurement is repeated until the angle of rotation is judged effective.

It is preferable that when the number of the repeated measurement exceeds a prescribed number, the measurement action is stopped to stop the polarimetry for the sample.

It is preferable that at least one measuring point "Pj" (Xj, Yj), where Xj≠Xi, other than the two measuring points "Pi" (Xi, Yi) is measured in the repeated measurement.

It is preferable that the polarization direction "X" of the incident light is discretely changed into two polarization signals "Xi".

It is preferable that a line connecting the two measuring points "P1" (X1, Y1) and "P2" (X2, Y2) is calculated on the basis of the equation (5):

$$Y=E+F\times X \quad (5)$$

where "Y" denotes a variable indicating the demodulation signal, "E" denotes a constant calculated, "F" denotes another constant calculated and "X" denotes a variable indicating the polarization direction, "X" is calculated from "E", "F" and a prescribed "Y" of the line to calculate the angle of rotation attributed to the sample on the basis of the "X".

It is preferable that the calculated angle of rotation is judged effective when the "F" is not less than a prescribed minimum value or not more than a prescribed maximum value.

It is preferable that the prescribed maximum value of the "F" is one calculated when a sample having a maximum transmittance is measured out of samples to be measured.

Further, the present invention also relates to a method of polarimetry by applying a magnetic field to a sample containing a spontaneously optical active substance and a magneto-optical active substance, allowing a light with a known polarization direction "X" to be incident upon the sample, changing and modulating s polarization direction of a light transmitted through the sample, and calculating an angle of rotation attributed to the sample on the basis of a magnitude of the magnetic field when an amount of change in an angle of rotation attributed to the spontaneously optical active substance and an amount of change in an angle of rotation attributed to the magnetic field satisfy a prescribed relation, the method comprising the steps of:

changing and modulating the polarization direction "X" of the incident light by applying the magnetic field;

detecting only a polarized component in a specific direction out of the light transmitted through the sample by a photosensor to obtain an output signal;

performing a phase sensitive detection on the output signal by using a signal for the modulating as a reference signal to obtain a demodulation signal "Y"; and calculating an angle of rotation from two measuring points "Pi" (Xi, Yi) obtained from the magnetic field strengths "Xi", where i denotes 1 and 2, corresponding to two polarization signals discretely selected from the polarization direction "X", and two demodulation signals "Yi", where i denotes 1 and 2, respectively corresponding to the magnetic field strengths "Xi".

It is preferable that at least one measuring point "Pi" out of the two measuring points "Pi" (Xi, Yi) is measured repeatedly when the calculated angle of rotation is judged not effective, to calculate again the angle of rotation on the basis of the measuring point "Pi" (Xi, Yi) measured repeatedly, and the measurement is repeated until the angle of rotation is judged effective.

It is preferable that when the number of the repeated measurement exceeds a prescribed number, the measurement action is stopped to stop the polarimetry for the sample.

It is preferable that at least one measuring point "Pj" (Xj, Yj), where Xj≠Xi, other than the two measuring points "Pi" (Xi, Yi) is measured in the repeated measurement.

It is preferable that the magnetic field strength is discretely changed into two magnetic field strengths.

It is preferable that a line connecting the two measuring points "P1" (X1, Y1) and "P2" (X2, Y2) is calculated on the basis of the equation (5):

$$Y=E+F\times X \quad (5)$$

where "Y" denotes a variable indicating the demodulation signal, "E" denotes a constant calculated, "F" denotes another constant calculated and "X" denotes a variable indicating the polarization direction.), "X" is calculated from "E", "F" and a prescribed "Y" of the line to calculate the angle of rotation attributed to the sample on the basis of the "X".

It is preferable that the calculated angle of rotation is judged effective when the "F" is not less than a prescribed minimum value or not more than a prescribed maximum value.

It is preferable that the prescribed maximum value of the "F" is one calculated when a sample having a maximum transmittance is measured out of samples to be measured.

For performing repeatedly the measurement again in the foregoing method of polarimetry, the repeated measurement includes the steps of; (1) measuring again at least one measuring point "Pi" out of the n (n is 2, or not less than 3) measuring points "Pi" (Xi, Yi); (2) calculating a regression line or line represented by the equation (1) or the equation (5) on the basis of the result measured again; (3) calculating the "B", "F", "C", "D" and/or "R"; (4) judging the effectiveness of the measurement result; and (5) repeating the steps (1) to (4) until the measurement result is judged effective when the previous measurement result is judged not effective in the step (4). Then, the angle of rotation attributed to the sample is obtained on the basis of the measurement result judged effective in the step (4). It is preferable that when the number of repeated measurements exceeds a prescribed number, the measurement action is stopped to stop the polarimetry for the sample.

Further, if a urine is used as the sample in the method of polarimetry of the present invention, it is possible to measure the angle of rotation attributed to the urine, particularly the concentrations of spontaneously optical active substances in the urine. Namely, it is possible to apply the method of polarimetry in accordance with the present invention to a method of urinalysis.

While the novel features of the invention are set forth particularly in the appended claims, the invention, both as to organization and content, will be better understood and appreciated, along with other objects and features thereof, from the following detailed description taken in conjunction with the drawings.

BRIEF DESCRIPTION OF THE SEVERAL VIEWS OF THE DRAWING

FIG. 3 is a diagram showing the configuration of another measuring apparatus to be used for carrying out a method of the present invention;

FIG. 4 is a graph showing the relation between the drive current and the demodulation signal in Example 2;

DETAILED DESCRIPTION OF THE INVENTION

The present invention pertains to a method of polarimetry by allowing a light with a known polarization direction to be incident upon a sample (specimen to be detected) in the form of fluid such as liquid or solution, detecting a polarization direction of a light transmitted through the sample, and measuring an angle of rotation of a polarization direction in the sample on the basis of the difference between the polarization directions of the incident light and the transmitted light.

Then, in this method, the polarization direction "X" of the light incident upon the sample is continuously or discretely changed, and simultaneously the polarization direction of the light incident upon the sample is modulated. Thus, only a polarized component in a specific direction out of the light transmitted through the sample is detected by a photosensor. Then, a phase sensitive detection is performed on the resulting output signal by using a signal for the modulation of the polarization direction as a reference signal to obtain a demodulation signal "Y". Then, the angle of rotation is calculated on the basis of the relation between the "X" and the "Y".

In concrete, the present invention provides a method of polarimetry for calculating the angle of rotation from n measuring points "Pi" (Xi, Yi) wherein "Xi" denotes X1, X2, . . . Xn obtained by discretely selecting n "Xs", where n denotes an integer of 2 or not less than 3, from the polarization direction "X", and "Yi" denotes demodulation signals "Yi" corresponding to their respective polarization signals Xi.

Further, if a urine is used as the sample in the method of polarimetry described above, it is possible to provide a method of urinalysis for detecting the concentration of a spontaneously optical active substance in the urine with efficiency.

Figure 1:
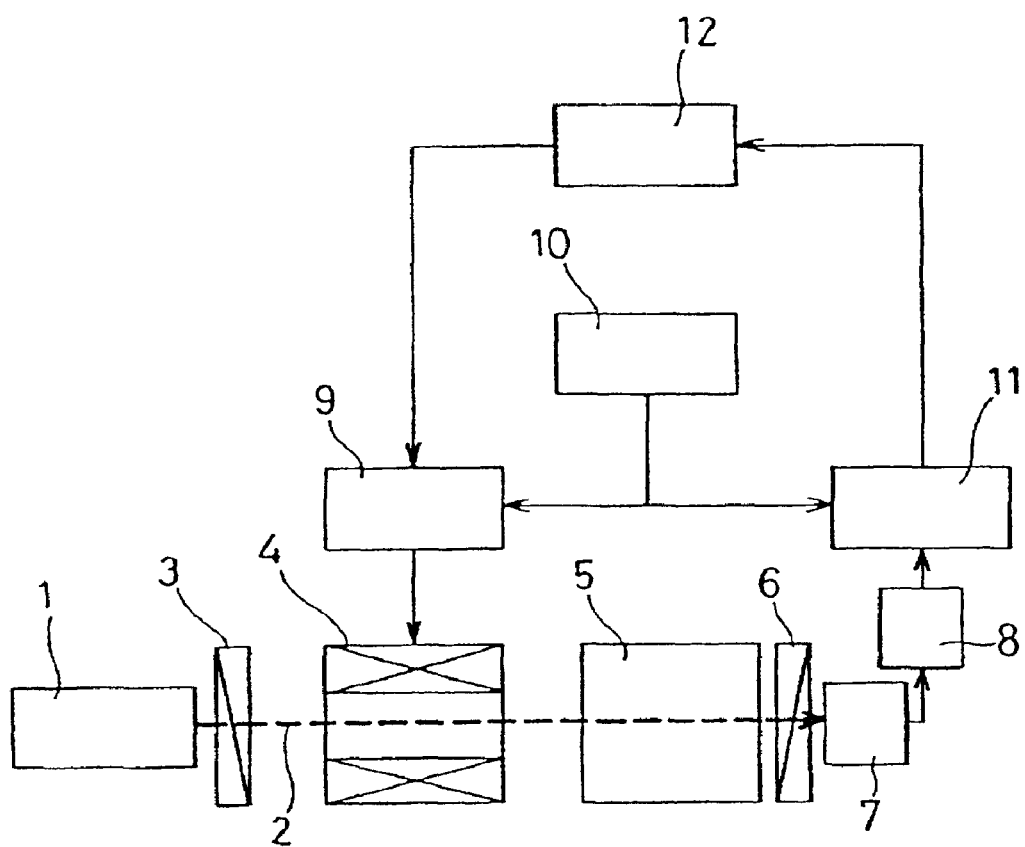
FIG. 1 is a diagram showing the configuration of one example of a measuring apparatus to be used for carrying out a method of the present invention.

Herein, a measuring apparatus usable for carrying out the method of the present invention will be described. FIG. 1 is a diagram showing the configuration of one example of a measuring apparatus to be used for carrying out the method of the present invention. In the apparatus shown in FIG. 1, a semiconductor laser module 1 projects, for example, a substantially parallel light 2 having a wavelength of 780 nm and an intensity of 3.0 mW.

A polarizer 3 transmits only a light having a polarized component parallel to the plane of a sheet of paper of this instant application. A Faraday cell 4 sweeps the polarization direction of the substantially parallel light 2 due to the optical Faraday effect, while modulating it.

Further, in a sample cell 5 accommodating a sample, the substantial optical path length is set to be, for example, 50 mm. An analyzer 6 is set so as to transmit only a light of a polarized component substantially perpendicular to the plane of a sheet of paper of this instant application. A photosensor 7 detects the substantially parallel light 2 transmitted through the analyzer 6.

Further, the apparatus has a preamplifier 8 for amplifying the output from the photosensor 7, a Faraday cell driver 9 capable of injecting a modulation signal current and a sweeping current to the Faraday cell 4, a signal generator 10 for supplying a modulation signal to the Faraday cell driver 9, and a lock-in amplifier 11 for conducting a phase sensitive detection on the output from the preamplifier 8 by using the modulation signal supplied to the Faraday cell as a reference signal.

The output signal from the lock-in amplifier 11 is a demodulation signal, and corresponds to the "S" in the equation (9). Therefore, the output signal from the lock-in amplifier 11 shows a first-order line with respect to the sweeping current of the Faraday cell driver, in principle.

Further, a computer 12 records and analyzes the output from the lock-in amplifier 11, i.e., the demodulation signal, while supplying a sweeping current signal to the Faraday cell driver 9, to calculate the angle of rotation.

Below, the present invention will be more specifically described by reference to the drawings and by way of examples, which should not be construed as limiting the scope of the invention.

EXAMPLE 1

In the measuring apparatus shown in FIG. 1, a substantially parallel light 2 having a wavelength of 780 nm and an intensity of 3.0 mW was projected, and the substantial optical path length of the sample cell 5 was set to be 50 mm. Thus, the angles of rotation attributed to pure water and a glucose aqueous solution having a concentration of 1000 mg/dl were measured in the following manner.

Incidentally, this example was carried out under such condition that the output signals from the lock-in amplifier 11, i.e., the demodulation signals became zero when an injection current into the Faraday cell was 0.0 A for the pure water, and when an injection current into the Faraday cell was 0.051 A for the glucose aqueous solution with a concentration of 1000 mg/dl, respectively. These injection currents were assumed to be standards.

In first, the injection current was swept in a range from −0.06 A to 0.06 A for 60 seconds, while injecting a modulation current with an amplitude of 0.001 A and a frequency of 1.3 KHz into the Faraday cell 4. The relation between the injection current and the output from the lock-in amplifier 11, i.e., the demodulation signal was shown by a solid line in FIG. 2. The results for the pure water and for the glucose aqueous solution were indicated by the marks "●" and "■", respectively. The relation between the injection current and the demodulation signal in Example 1 was shown in FIG. 2.

The time constant of the lock-in amplifier was set as follows. In first, the time constant was set to be sufficiently shorter as compared with the sweep time, i.e., about 3 mS, which was larger than the modulation period, and the injection current was swept to obtain the relation with the demodulation signal, i.e., each solid line of FIG. 2. Then, the time constant was gradually increased to obtain the solid line of FIG. 2, during which the time constant immediately before the resulting solid line would deviate from the previously obtained solid line was confirmed.

Herein, the term "deviate" denotes "reduce in gradient". By performing these steps, it is possible to achieve the highest S/N ratio with respect to the length of time required for sweeping. Herein, the time constant was set at 100 mS.

Figure 2:
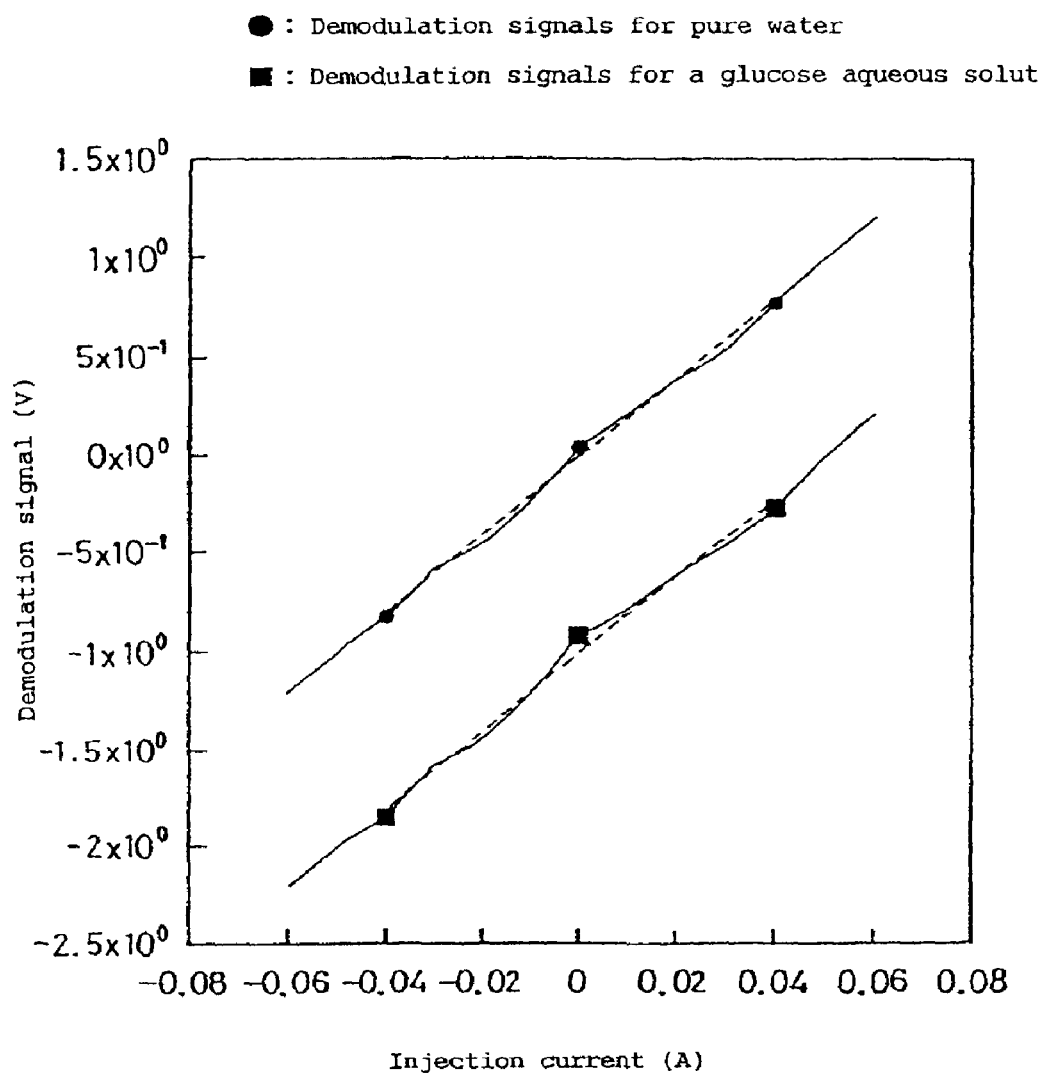
FIG. 2 is a graph showing the relation between the injection current and the demodulation signal in Example 1.

Each of the solid lines of FIG. 2 should be a straight line as shown by the equation (10) in principle. However, in actuality, the solid line deviates from the straight line due to the superimposition of various noises. The injection currents "X0" when the demodulation signals become zero read from their respective solid lines are $X_0 \approx -0.002$ (A) and $X_0 \approx 0.05$ (A) for the pure water and the glucose aqueous solution, respectively.

Further, assuming that three points when the injection currents were −0.04 A, 0 A, and 0.04 A were selected points, the injection currents and the demodulation signals thereof were shown in Table 1.

TABLE 1

| Injection current Xi(A) | Demodulation signal for pure water Yi(V) | Demodulation signal for glucose aqueous solution Yi(V) |
|---|---|---|
| X1 = −0.04 | Y1 = −0.82 | Y1 = −1.85 |
| X2 = 0 | Y2 = 0.05 | Y2 = −0.92 |
| X3 = 0.04 | Y3 = 0.78 | Y3 = −0.26 |

Herein, by using the injection currents as criterion variables "Xi" and the demodulation signals as dependent variables "Yi", the linear regression treatment was performed on the basis of the principle of a least squares method. Consequently, the regression lines shown in the following equation (11):

$$Y \approx 0.00333 + 20 \times X \tag{11}$$

and the following equation (12):

$$Y \approx -1.01 + 19.9 \times X \tag{12}$$

were obtained for the pure water and the glucose aqueous solution, respectively. These were indicated by dotted lines in FIG. 2.

The injection currents "$X_0$" when the demodulation signals "Y" became zero were calculated from these respective regression line to give $X_0 \approx -0.000167$ (A) and $X_0 \approx 0.0508$ (A) for the pure water and the glucose aqueous solution, respectively. These values denoted their respective angles of rotation, and were closer to the true numerical values set than the numerical values read from the solid lines, resulting in an improved measurement precision than in the case of reading from the solid lines of FIG. 2.

Then, the sum "C" of squares of deviation was determined on the basis of the data shown in Table 1 by using the equations (2), (11), and (12) to give $C \approx 3.27 \times 10^{-3}$ and $C \approx 1.22 \times 10^{-2}$ for the pure water and the glucose aqueous solution, respectively.

These values served as indexes for the fit thereof with their respective regression lines shown by the equations (11) and (12). Namely, this indicated that, the smaller the value of "C" was, the higher the fit with respect to the regression line was.

Then, shown in Table 2 were the data when microparticles such as bubbles and dust entered the inside of the aqueous solution in the optical path for the substantially parallel light 2 in measuring the glucose aqueous solution, so that a large noise was mixed in the demodulation signal.

TABLE 2

| Injection current Xi(A) | Demodulation signal for glucose aqueous solution Yi(V) |
|---|---|
| X1 = −0.04 | Y1 = −2.05 |
| X2 = 0 | Y2 = −0.92 |
| X3 = 0.04 | Y3 = −0.26 |

The data shown in Table 2 were obtained when a noise was mixed at a injection current of around −0.04 A, so that the noise superimposed only on the demodulation signal Y1 at X1=−0.04. At this step, the regression line was expressed as the following equation (13):

$$Y \approx -1.08 + 22.4 \times X \tag{13}$$

In accordance with the regression line expressed by the equation (13), the injection current "$X_0$" when the demodulation signal "Y" became zero was calculated to give $X_0 \approx 0.0482$ (A) for the glucose aqueous solution. This value denoted the angle of rotation, and indicated the adverse effect of an increase in an error due to the mixing of noises as distinct from the value calculated from the equation (12).

Then, the sum "C" of squares of deviation was determined on the basis of the data shown in Table 2 by using the equations (2) and (13) to give $C \approx 8.62 \times 10^{-2}$. This value of "C" was larger than the value of "C" determined on the basis of the data shown in Table 1 from the equation (12), indicating a low fit with respect to the regression line.

When the sum "C" of squares of deviation is larger than a prescribed numerical value, for example, assuming that the prescribed maximum value was $2.0 \times 10^{-2}$, the measurement could be judged effective in case of $C \leq 2.0 \times 10^{-2}$. In other words, by judging the measurement result ineffective in case of $C > 2.0 \times 10^{-2}$, it was possible to detect the mixing of noises, and as a result, it was possible to find out the low-precision measurement result.

When a large number of bubbles were mixed and the measurement was judged ineffective, the glucose aqueous solution was measured again in the following manner. The selected points of the injection current were set at −0.04 A, 0 A, and 0.04 A, and the same values of Y1, Y2, and Y3 as shown in Table 1 were obtained. From these values, the equation (12) was properly obtained to give $C \approx 1.22 \times 10^{-2}$.

This value was not more than the prescribed maximum value=$2.0 \times 10^{-2}$, and hence it was possible to judge the measurement effective.

Incidentally, in this example, it was possible to obtain the effective measurement result by repeatedly performing the measurement once. However, it is possible to repeatedly perform remeasurement until an effective result is obtained. In this step, by setting the maximum number of repetitions of the remeasurement to a prescribed value, and by setting the computer or the like to stop the measurement action when the number of repetitions thereof exceeds the prescribed value, the infinite loop can be practically inhibited.

As described above, at least 3 points of the injection currents are selected to be used as criterion variables "Xi" and the demodulation signals corresponding thereto are used as dependent variables "Yi", and the linear regression treatment is performed on the basis of the principle of a least squares method to obtain a regression line. Consequently, it is possible to calculate the injection current "$X_0$" which corresponds to a demodulation signal "Y" of zero, and as a result, it is possible to measure the angle of rotation with more precision.

Further, the sum "C" of squares of deviation is calculated by using the equation (2). When the sum "C" of squares of deviation is not more than the prescribed maximum value, the measurement result is judged effective. Consequently, it is possible to find out the measurement result having a large error due to influences of microparticles such as bubbles and dust, and noises.

Herein, by repeating the measurement until the measurement result is judged effective when the measurement is judged ineffective, the measurement result with ensured reliability can be obtained. When microparticles such as bubbles and dust are suspended, the high-reliability result to be judged effective will be obtained sometime by repeating the measurement in this manner as minimum as possible.

However, when there are a very large number of microparticles such as bubbles and dust, the maximum number of repetitions of the remeasurement is set as a prescribed value, and the computer or the like is set such that the measurement action is stopped when the number of repetitions thereof exceeds the prescribed value. Such setting is practical because it can limit the measurement time. Further, it is practical because it can inhibit the possible infinite loop.

As described above, in accordance with this example, it is possible to measure the angle of rotation with high precision. In addition, the sureness that the high-reliability measurement result can be obtained is increased. The practical effect thereof is very large.

EXAMPLE 2

Example 2 of the present invention will be described by reference to FIGS. 3 and 4. FIG. 3 is a diagram showing the configuration of a measuring apparatus used in this example, and reference numerals 1 to 3 and 6 to 12 are the same as those in the measuring apparatus shown in FIG. 1.

On a sample cell 13 accommodating a sample, a solenoid coil was wound so that it would be possible to apply a magnetic field to the sample along the transmission direction of a substantially parallel light 2. The substantial optical path length was set to be 50 mm. This was for controlling the current to be flown through the solenoid coil while modulating it by the use of the optical Faraday effect of the sample, and thereby controlling the polarization direction of the substantially parallel light 2, while modulating it. Incidentally, the basic principle of the method in which the angle of rotation is measured by the Faraday effect of the sample itself in this manner is described in the specification of Laid-open Japanese Patent Publication No. Hei 09-145605.

A modulation signal current and a control current were injected into the sample cell 13 by a Faraday cell driver 9.

In the measuring apparatus shown in FIG. 3, similarly with the measuring apparatus shown in FIG. 1, the output signal from a lock-in amplifier 11 was a demodulation signal, and corresponded to the "S" of the equation (10). Therefore, the output signal from the lock-in amplifier 11 showed a first-order line with respect to the control current of the Faraday cell driver 9 in principle.

By using the measuring apparatus shown in FIG. 3, the angles of rotation attributed to pure water, and glucose aqueous solutions with respective concentrations of 1000 mg/dl and 2000 mg/dl were measured in the following manner.

Incidentally, this example was carried out under such condition that the output signals from the lock-in amplifier 11, i.e., the demodulation signals became zero, when the injection current into the solenoid coil of the sample cell was 0.02 A for the pure water, when the injection current into the solenoid coil of the sample cell was 1.01 A for the glucose aqueous solution with a concentration of 1000 mg/dl, and when the injection current into the solenoid coil of the sample cell was 2.00 A for the glucose aqueous solution with a concentration of 2000 mg/dl. These were assumed to be standards.

In first, while injecting a modulation current with an amplitude of 0.001 A and a frequency of 1.3 KHz into the solenoid coil 13, the current was varied discretely to −1.5 A, 0.0 A, and 1.5 A in 1.5 A intervals for every second. In this step, the time constant of the lock-in amplifier was set to be 100 mS.

The output signal from the lock-in amplifier 11 after an elapse of the time from immediately after setting of each injection current until the demodulation signal asymtotically approached a certain value to show no change, i.e., after an elapse of the time of one second which was 7 to 8 times or more the time constant was shown as the demodulation signal with respect to the injection current in Table 3 and FIG. 4.

In FIG. 4, the demodulation signals for the pure water, the glucose aqueous solution with a concentration of 1000 mg/dl, and the glucose aqueous solution with a concentration of 2000 mg/dl were denoted by the marks "○", "●", and "■", respectively.

TABLE 3

| Injection current $X_i$(A) | Demodulation signal for pure water $Y_i$(V) | Demodulation signal for glucose aqueous solution $Y_i$(V) conc. 1000(mg/dl) | Demodulation signal for glucose aqueous solution $Y_i$(V) conc. 2000(mg/dl) |
|---|---|---|---|
| −1.5 | −0.304 | −0.480 | −0.700 |
| 0.0 | 0.040 | −0.205 | −0.320 |
| 1.5 | 0.290 | 0.107 | −0.085 |

Herein, by using the injection currents as criterion variables "$X_i$" and the demodulation signals as dependent variable "$Y_i$", the linear regression treatment was performed on the basis of the principle of a least squares method. Consequently, the regression lines shown in the following equation (14):

$$Y \approx 0.00867 + 0.198 \times X \quad (14),$$

the following equation (15):

$$Y \approx -0.193 + 0.196 \times X \quad (15),$$

and the following equation (16):

$$Y \approx -0.368 + 0.205 \times X \quad (16)$$

were obtained for the pure water and the glucose aqueous solutions with respective concentrations of 1000 mg/dl and 2000 mg/dl, respectively.

The injection currents "$X_0$" when their respective demodulation signals "Y" became zero were calculated by using these respective regression lines to give $X_0 \approx -0.0438$ (A), $X_0 \approx 0.985$(A) and $X_0 \approx 1.80$ (A) for the pure water and the glucose aqueous solutions with respective concentrations of 1000 mg/dl and 2000 mg/dl, respectively. These denoted their respective angles of rotation.

Then, their respective correlation coefficients "R" were determined on the basis of the data shown in Table 3 by using the equations (4), (14), (15) and (16) to give R≈0.0996, R≈0.999 and R≈0.991 for the pure water and the glucose aqueous solutions with respective concentrations of 1000 mg/dl and 2000 mg/dl, respectively.

These values served as indexes for the fit thereof with respect to their respective regression lines respectively shown by the equations (14), (15), and (16). Namely, this indicated that, the closer to 1 the value of "R" was, the higher the fit with respect to the regression line was.

Herein, the difference $\Delta X_0$ between the injection current when the set demodulation signal became zero and the injection current calculated from the respective regression line expressed respectively by the equation (14), (15) or (16) was determined. There were obtained $\Delta X_0$=−0.0638 (A), $\Delta X_0$=−0.025 (A) and $\Delta X_0$=−0.2 (A) for the pure water and the glucose aqueous solutions with their respective concentrations of 1000 mg/dl and 2000 mg/dl, respectively. Therefore, the closer to 1 the value of "R" was, the closer to 0 the value of "$\Delta X_0$" was, indicating that the precision of the measurement was high.

When the correlation coefficient "R" was not less than the prescribed minimum value, for example, in case of R≧0.995, the measurement was judged effective. In other words, in case of R<0.995, the measurement result was judged ineffective. Consequently, it was possible to find out the low-precision measurement result, and hence it was possible to ensure the precision of the measurement result.

Herein, the measurement was performed again for the glucose aqueous solution with a concentration of 2000 mg/dl, of which the previous measurement result was judged ineffective. At this step, for simplification, the measurement was performed at an injection current Xi of 0.0 (A). This was attributable to the following fact. Namely, in the state where measurement was stopped, the injection current into the solenoid coil was zero and, therefore, in consideration of the inductance thereof, a prescribed injection current could be reached in the shortest time. Measurement was performed in the same manner as described above to give a demodulation signal Yi of −0.35 (V).

On the basis of the data shown in Table 3, a regression line was calculated from Xi=−1.5 and 1.5, and Yi corresponding thereto, to obtain the following equation (17):

$$Y \approx -0.378 + 0.205 \times X \quad (17)$$

By using these, the correlation coefficient "R" was calculated to give R≈0.997. This value satisfied R≧0.995, so that it was possible to judge the measurement effective.

The injection current "$X_0$" when the demodulation signal "Y" became zero was calculated to give $X_0$≈1.84 (A) for the glucose aqueous solution with a concentration of 1000 mg/dl. This denoted the angle of rotation. This gave $\Delta X_0$=−0.16 (A), indicating that the precision was improved as compared with the first measurement. Thus, by performing the measurement again, the closer to 1 the value of "R" became, the closer to 0 the value of "$\Delta X_0$" was, indicating that the precision is improved.

As described above, the injection current is discretely changed to at least 3 points, and these are used as criterion variables "Xi" and the demodulation signals corresponding thereto are used as dependent variables "Yi", and the linear regression treatment was performed on the basis of the principle of a least squares method to obtain a regression line. Consequently, it is possible to calculate the injection current "$X_0$" which corresponds to the demodulation signal "Y" of zero, and as a result, it is possible to measure the angle of rotation with more precision.

Further, the correlation coefficient "R" is calculated by using the equation (4). When the correlation coefficient "R" is not less than the prescribed minimum value, the measurement result is judged effective. Consequently, it is possible to find out the measurement result having a large error due to noises.

For the measurement result providing a correlation coefficient "R" of not more than the prescribed minimum value, the demodulation signal corresponding to at least one injection current is measured repeatedly again. This repeatedly measured value and the previously measured value are combined to calculate a regression line again, and also calculate a correlation coefficient "R" again. If the correlation coefficient "R" is not less than the prescribed minimum value, the measurement result is judged effective. Thus, by repeatedly performing the measurement, it is possible to obtain an effective measurement result with efficiency. Further, the value of "β" (corresponding to the injection current) is not required to be changed continuously so that "S" becomes zero as in the prior art, resulting in a simplified configuration of a circuit.

Further, in this example, the injection current "X0" when the demodulation signal "Y" becomes zero is calculated by extrapolation from the regression line. Therefore, it is not necessary to actually inject such a current which enables the demodulation signal to become 0. Accordingly, it is possible to set large the measurable concentration range of the sample.

Incidentally, in Example 1, the overall time taken to sweep the injection current is required to be sufficiently longer as compared with the time constant of the lock-in amplifier. Therefore, a longer measurement time than that in this example is required for ensuring an S/N ratio comparable to that in this example.

In this example, the period of time from the start of injecting the injection current at each discrete measuring point to the determination of the demodulation signal may be set to be (7 to 8 times) larger than the time constant of the lock-in amplifier, so that the measurement time can be shorten.

As described above, in accordance with this example, it is possible to measure the angle of rotation in a wide concentration range with high precision and in a short time. Further, by detecting the measurement result having a large error, it is possible to ensure the precision. Further, by performing the measurement again, it is possible to obtain an effective measurement result with efficiency, and the practical effect thereof is very large.

EXAMPLE 3

In this example, for shortening the measurement period of time, the injection current was discretely set at two points "X1" and "X2". These "X1" and "X2" and the demodulation signals "Y1" and "Y2" respectively corresponding thereto were used to calculate a line. It was possible to calculate the injection current "$X_0$" when the demodulation signal "Y" became zero from this line. Consequently, it was possible to measure the angle of rotation with high precision. The measuring apparatus shown in FIG. 3 was used in this example.

Further, in the same manner as in Example 2, this example was carried out under such condition that the output signals from the lock-in amplifier 11, i.e., the demodulation signals became zero, when the injection current into the solenoid coil of the sample cell was 0.02 A for the pure water, when the injection current into the solenoid coil of the sample cell was 1.01 A for a glucose aqueous solution with a concentration of 1000 mg/dl, and when the injection current into the solenoid coil of the sample cell was 2.00 A for a glucose aqueous solution with a concentration of 2000 mg/dl. These were assumed to be standards.

In the same manner as in Example 2, a modulation current having an amplitude of 0.001 (A) and a frequency of 1.3 KHz was injected into the solenoid coil 13. Herein, the injection current was set at −1.5 (A), then varied discretely to 1.5 A at an elapse of one second therefrom. Then, another one second was allowed to elapse. The output signal of the lock-in amplifier at an elapse of one second from the time when each of the injection currents was set at (X1=−1.5 or X2=1.5) was taken as demodulation signal (Y1 or Y2).

Herein, the time constant of the lock-in amplifier was set to be 100 mS. The measured values when the glucose aqueous solution with a concentration of 1000 mg/dl was measured are shown in Table 4.

TABLE 4

| Injection current $X_i(A)$ | Demodulation signal for glucose aqueous solution $Y_i(V)$ Conc. 1000 (mg/dl) |
|---|---|
| X1 = −1.5 | Y1 = −0.490 |
| X2 = 1.5 | Y2 = −0.105 |

Table 4 gave a line represented by the following equation (18):

$$Y \approx -0.193 + 0.198 \times X \quad (18)$$

In accordance with this line, the injection current "$X_0$" when the demodulation signal "Y" became zero was calculated to give $X_0 \approx 0.0975$ (A) for the glucose aqueous solution with a concentration of 1000 mg/dl. This denoted the angle of rotation.

Herein, the difference $\Delta X_0$ between the injection current when the set demodulation signal becomes zero and the injection current calculated from the line expressed by the equation (18) was calculated to give $\Delta X_0 = -0.035$ (A).

Even if the measurement was carried out at two measuring points in this manner, the measurement might be achieved with this degree of precision. The relation between the injection current and the demodulation signal at this step was indicated by the mark "●" of FIG. 5.

However, in the case of the two measuring points, even if the correlation coefficient "R" was calculated by using the equation (4), every correlation coefficient "R" became 1, and hence it could not be used for judgment of the measurement result.

Figure 5:
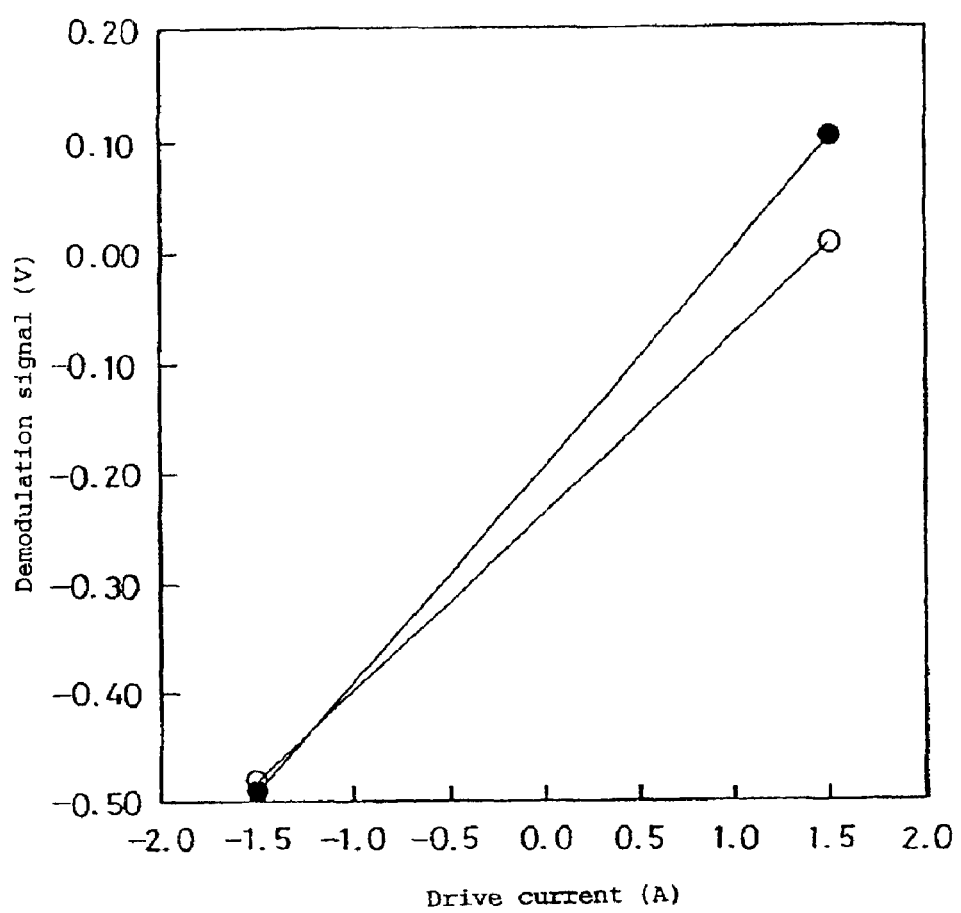
FIG. 5 is a graph showing the relation between the drive current and the demodulation signal in Example 3.

For example, the data when the measurement was performed by renewing the glucose aqueous solution with a concentration of 1000 mg/dl in the sample cell were ahown in FIG. 5. Herein, bubbles were mixed therein, and the data showed the example in which the bubbles entered the optical path for interference at an injection current of 1.5 A. The relation between the injection current and the demodulation signal at this step was indicated by the mark "○" of FIG. 5.

TABLE 5

| Injection current $X_i(A)$ | Demodulation signal for glucose aqueous solution $Y_i(V)$ Conc. 1000 (mg/dl) |
|---|---|
| X1 = −1.5 | Y1 = −0.480 |
| X2 = 1.5 | Y2 = −0.01 |

Table 5 gave a line represented by the following equation (19):

$$Y \approx -0.235 + 0.163 \times X \quad (19)$$

In accordance with this line, the injection current "$X_0$" when the demodulation signal "Y" became zero was calculated to give $X_0 \approx 1.44$ (A) for the glucose aqueous solution with a concentration of 1000 mg/dl. This denoted the angle of rotation.

Herein, the difference $\Delta X_0$ between the injection current when the set demodulation signal became zero and the injection current calculated from the line expressed by the equation (18) was calculated to give $\Delta X_0 = -0.43$ (A).

As described above, the error was larger than the case where the data shown in Table 4 was used, but detection could not be achieved with "R". In the equation (19), when the injection current was 1.5 A, bubbles entered the optical path, resulting in a reduction in the transmittance. This affected the coefficient of "X" (=0.163). In actuality, the coefficient of "X" was 0.198 in the equation (18), apparently indicating the difference therebetween. Herein, if the equation was judged effective when the coefficient of "X" was not less than a prescribed minimum value on the assumption that the prescribed minimum value of the coefficient of "X" was 0.18, the equation (18) was judged effective, but the equation (19) was judged not effective.

Thus, by judging effective the case where the coefficient of "X" was not less than a prescribed minimum value, it was possible to find out the measurement result having a large error due to noises occurred by entering of bubbles into the optical path, and the like. Consequently, it was possible to ensure the reliability of the measurement.

Herein, when the coefficient of "X" is not a prescribed minimum value or more, in the same manner as in Example 2, the measurement was performed repeatedly again on at least one point, and a line was calculated again on the basis of the measured value. Then, the effectiveness was judged again on the basis of the coefficient of "X" of the line. This operation was repeated until an effective measured result would be obtained.

In the foregoing example, the demodulation signal at the same injection current as that in the first measurement was used as a measured value in repeatedly performing the measurement again. Namely, the measurement was performed again for at least one value of "Xi" (injection current) out of the values of "Xi" in the first measurement.

However, when the measurement is performed again, it is not necessarily required to select the injection current from the values of "Xi" in the first measurement. The other value of "Xi" may be separately set when the measurement is performed again.

For example, in performing the measurement again, the measurement is performed at the time when the injection current Xi is 0.0 (A). This is attributable to the following fact. Namely, in the state where measurement is stopped, the injection current into the solenoid coil is zero. Therefore, in consideration of the inductance thereof, a prescribed injection current can be reached in the shortest time. This is advantageous for shortening the measurement time. Further, when a malfunction invariably occurring with respect to the same injection current and the like cause the noises, it may be possible to avoid the ineffective measurement by performing the measurement with a different injection current from that in the first measurement in this manner.

Thus, when the measurement is performed again, the measurement is performed with a different injection current from that in the first measurement. On the basis of this measured value and the first measured value, a line or a regression line is calculated. Accordingly, it is possible to judge the effectiveness from the coefficient of "X", and the like. As a result, it is possible to obtain an effective measurement result with efficiency.

As described above, in accordance with this example, it became possible to shorten the measurement time by performing the measurement at two points. For example, in this example, it is possible to perform the measurement for about 2 seconds. Further, it is possible to ensure the precision by detecting the measurement result having a large error. Further, it is possible to obtain an effective measurement result with efficiency by performing the measurement again, and the practical effect thereof is very large.

Incidentally, in this example, there was shown the example in which the effectiveness was judged by the coefficient corresponding to "X" of the line obtained by performing the measurement at two points. However, the same effect can be obtained even by measuring three or more points as in Example 2, forming a regression line, and performing the judgment by the coefficient corresponding to "X" thereof.

EXAMPLE 4

In this example, by using the measuring apparatus shown in FIG. 3 used in Example 2, the angles of rotation of urines as samples were measured, and the glucose concentrations, i.e., the urine sugar values were examined.

These urines were a urine 1 of which the glucose concentration had previously been measured to be 450 mg/dl, and a urine 2 of which the glucose concentration had previously been measured to be 655 mg/dl, by a urinalysis apparatus. Further, both were judged to have a concentration of albumin, which was a protein in a urine, of 10 mg/dl or less.

Figure 6:
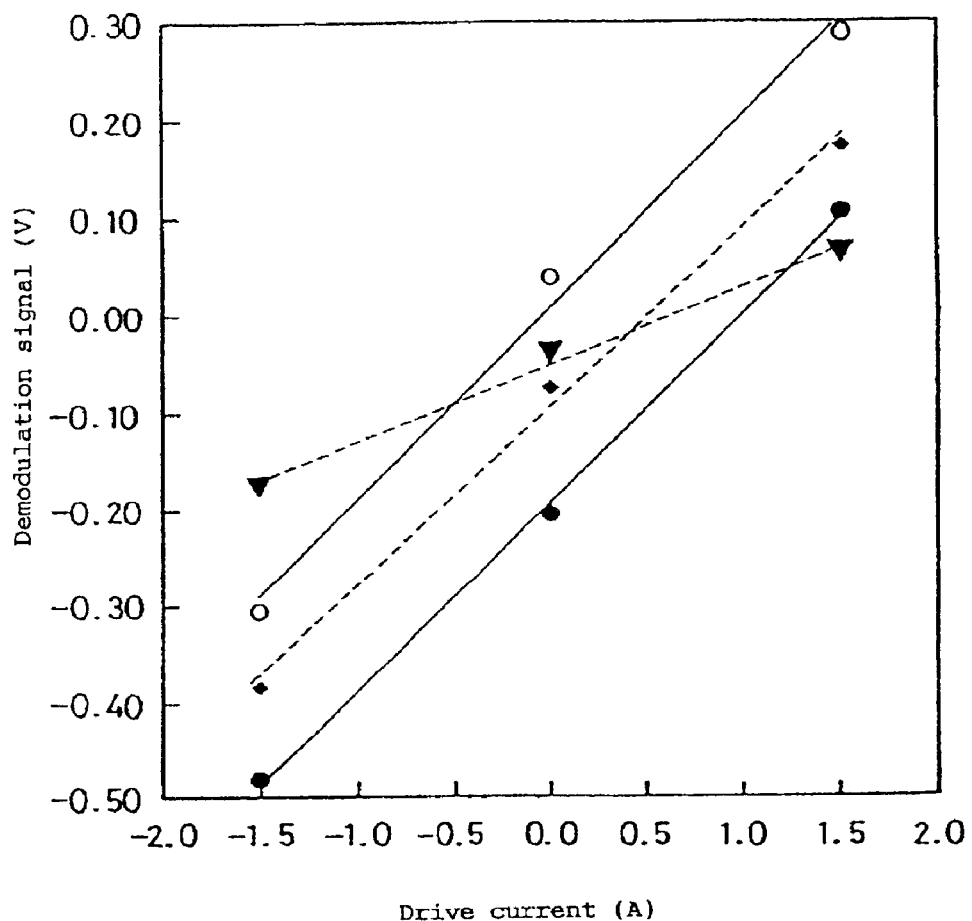
FIG. 6 is a graph showing the relation between the drive current and the demodulation signal in Example 4.
Figure 7:
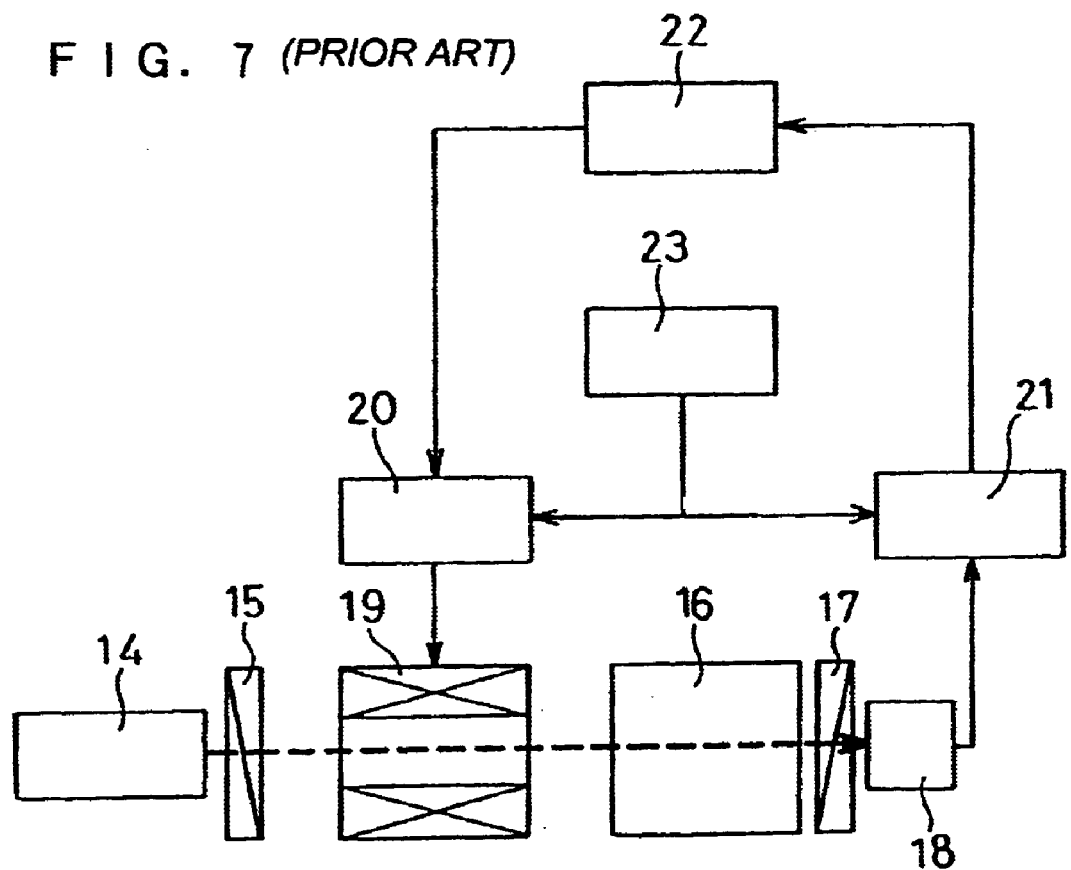
FIG. 7 is a diagram showing the configuration of one example of a conventional polarimeter.

The results of the measurement of the angles of rotation for the urines 1 and 2 were shown in FIG. 6 and Table 6. The results for the pure water and the glucose aqueous solution with a concentration of 1000 mg/dl shown in Example 2 were shown in FIG. 6.

Herein, in the same manner as in Example 2, by using the injection currents as criterion variables "Xi" and the demodulation signals as dependent variables "Yi", the linear regression treatment was performed on the basis of the principle of a least squares method. Consequently, the regression lines shown in the following equation (20):

$$Y \approx -0.0924 + 0.185 \times X \quad (20)$$

and the following equation (21):

$$Y \approx -0.0485 + 0.0803 \times X \quad (21)$$

were obtained for the urines 1 and 2, respectively.

TABLE 6

| Injection current Xi(A) | Demodulation signal for pure water Yi(V) | Demodulation signal for glucose aqueous solution Yi(V) 1000 (mg/dl) | Demodulation signal Yi(V) Urine 1 | Demodulation signal Yi(V) Urine 2 |
|---|---|---|---|---|
| −1.5 | −0.304 | −0.480 | −0.380 | −0.175 |
| 0.0 | 0.040 | −0.205 | −0.0722 | −0.0365 |
| 1.5 | 0.290 | 0.107 | 0.175 | 0.0660 |

The injection currents "$X_0$" when the demodulation signals became zero were calculated from their respective regression lines to give $X_0 \approx 0.499$ (A) and $X_0 \approx 0.604$ (A) for the urines 1 and 2, respectively. These denoted angles of rotation, and from these, the glucose concentrations "Co" were calculated by the following equation (22):

$$Co = (X_0 - X_0(GLO)) \times 1000 / (X_0(GL1000) - X_0(GLO)) \quad (22)$$
$$= (X_0 - 0.02) \times 1000 / 0.99 \text{ (mg/dl)}$$

where $X_0(GLO)$ denotes an injection current set so that a demodulation signal for pure water becomes zero, and $X_0(GL1000)$ denotes an injection current set so that a demodulation signal for the glucose aqueous solution with a concentration of 1000 mg/dl becomes zero, to give the glucose concentrations of the urines, i.e., the urine sugar value UG1≈484 (mg/dl) and the urine sugar value UG2≈590 (mg/dl). These values indicated that it was possible to perform the measurement with higher precision for the urine 1.

For showing the relation between the measurement precision, and the sums "C" and "D" of squares of deviation, and the correlation coefficient "R", by using the equations (2), (3), and (4), respective sums "C" and "D" of squares of deviation, and respective correlation coefficients "R" for pure water, the glucose aqueous solution with a concentration of 1000 (mg/dl), and the urines 1 and 2 were determined on the basis of the data shown in FIG. 6, and the equations (14), (15), (20), and (21). The results were shown in Table 7.

TABLE 7

|  | Pure water | Glucose aqueous solution of 1000 (mg/dl) | Urine 1 | Urine 2 |
|---|---|---|---|---|
| C | $1.47 \times 10^{-3}$ | $2.28 \times 10^{-3}$ | $6.12 \times 10^{-4}$ | $2.16 \times 10^{-4}$ |
| D | $8.32 \times 10^{-3}$ | $8.03 \times 10^{-3}$ | $3.46 \times 10^{-3}$ | $5.98 \times 10^{-3}$ |
| R | 0.996 | 0.999 | 0.998 | 0.996 |

Table 7 indicates that the urine 1 has an "R" closer to 1, and provides higher precision than the urine 2. The smaller the value of "C" is, the higher precision it shows. However, the smaller the absolute value of each demodulation signal is, the smaller the value of "C" tends to be. Therefore, the value of "C" is not suitable for comparison between the measurement results of the samples providing demodulation signals whose absolute values are largely different from each other.

Therefore, in the case where the absolute values of respective demodulation signals are largely different from each other as in this example, use of the numerical values corrected by the absolute values of the demodulation signals as "D" is more advantageous because the judgment can be carried out irrespective of the absolute values of the demodulation signals. In actuality, as shown in Table 7, the urine 2 has a smaller value of "C" than the "C" of the urine 1, but the precision is higher for the urine 1. This is because the transmittance is lower, and the absolute value of the demodulation signal is smaller for the urine 2.

Even in this case, "D" and "R" serve as indexes of the precision. Also in this example, when the measurement is judged by using "C", "D", "R" and/or "B" or "F", which is the coefficient of "X" not to be effective, the measurement is repeatedly performed again for at least one point. As a result, it is possible to obtain an effective measured value with efficiency while keeping the reliability of the measurement.

As described above, in accordance with this example, by using "D" or "R", it is also possible to judge the precisions of the measurement results of specimens providing demodulation signals whose absolute values are largely different from each other due to the influence of the transmittances and the like. Further, it is possible to nullify the measurement result with a large error, and the practical effect thereof is very large.

Further, it is possible to examine the glucose concentration of a urine of which albumin concentration is a normal value without the use of consumable articles such as test papers, and the effect thereof is large.

EXAMPLE 5

In this example, the measurement was performed for a glucose aqueous solution with a concentration of 2000 mg/dl by using the measuring apparatus shown in FIG. 3, and under the same conditions as in Example 2. In this example, large suspending particles entered the optical path at an injection current of 1.5 A, so that the transmitted light became substantially zero and the demodulation signal also became zero. The results were shown in Table 8.

TABLE 8

| Injection current $X_i$(A) | Demodulation signal for glucose aqueous solution $Y_i$(V) Conc. 1000 (mg/dl) |
|---|---|
| −1.5 | −0.700 |
| 0.0 | −0.320 |
| 1.5 | −0.00 |

On the basis of the data shown in Table 8, a regression line was calculated in the same manner as in Example 2 to give the following equation (23):

$$Y \approx -0.340 + 0.233 \times X \quad (23)$$

The injection current "$X_0$" when the demodulation signal became zero was calculated from the regression line represented by the equation (23) to give $X_0 \approx 1.46$ (A). This showed the angle of rotation.

By using the equation (4), the correlation coefficient "R" was determined from the equation (23) to give $R \approx 0.999$. This served as an index for the fit thereof with respect to the regression line. Namely, this indicated that, the closer to 1 the value of "R" was, the higher the fit with respect to the regression line was.

The difference $\Delta X_0$ between the injection current when the set demodulation signal becomes zero and the injection current calculated from the regression line expressed by the equation (23) was calculated to give $\Delta X_0 = -0.54$.

Herein, in comparison with $R \approx 0.991$ and $\Delta X_0 = -0.2$ (A) calculated from the equation (16) of Example 2, the equation (23) yielded the value of "R" closer to 1, but a larger error, i.e., a larger absolute value of $\Delta X_0$. This phenomenon occurred due to the relation between the timing at which suspending particles entered the optical path and the relative position of the injection current.

Thus, even when suspending particles entered the optical path, if the timing and the relative position of the injection current were different, the error might affect the correlation coefficient "R". For example, when suspending particles entered the optical path at an injection current of 0 (A), the demodulation signal herein occurred became roughly zero, and the value of "R" went away from 1. Therefore, it was possible to detect the increase in the error.

The increase in the error due to noises caused by suspending particles might not affect the correlation coefficients "R", "C" and "D". Therefore, if the effectiveness was judged on the basis of only the values of "C", "D", and/or "R", there might occur a problem that the measurement result having a large error was judged effective.

Under such circumstances, a prescribed maximum value of the coefficient of "X" was set, and the condition that the measurement result was judged effective when the coefficient was not more than the maximum value was added, making it possible to avoid the problem.

It was reasonable to use the coefficients "B" and "F" of "X" obtained for a sample having the largest transmittance out of the samples to be measured. This was because there was no possibility in principle that a larger coefficient than the coefficient of "X" for the solution to be detected having the largest transmittance was obtained. Namely, apparent from the equation (10), when the intensity ($I_0$) of light incident upon a simple and the modulation amplitude (6) were constant, the coefficient of "X" was unambiguously determined by the transmittance (T) of the sample.

Therefore, if the prescribed maximum value was set to be 0.21 from the equations (14), (15), and (16) obtained for the cases where the obstruction due to large suspending particles was not observed, the equation (23) was not judged effective, making it possible to detect the obstruction. In other words, when the coefficient of "X", such as "B" or "F" was larger than 0.21, the measurement result was judged ineffective. As a result, it was possible to find out the low-precision measurement result, and it was possible to ensure the precision of the measurement result.

Incidentally, when the number of the measuring points is two, it is also possible to allow the same operation by forming a line, and setting a prescribed maximum value for the coefficient "F" of the value of "X" (corresponding to the gradient).

As described above, in accordance with the present invention, the configuration of a circuit is simplified, the measurement time is constant, and the precision of the measurement result can be found. As a result, it is possible to judge whether the result is effective or ineffective. Further, it is possible to obtain an effective measurement result with efficiency. Consequently, it is possible to implement a high-reliability low-priced method of polarimetry which can be accomplished by using a compact apparatus, and the practical effect thereof is very large.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A method of polarimetry by allowing a light with a known polarization direction "X" to be incident upon a sample, detecting a polarization direction of a light transmitted through said sample, and measuring an angle of rotation of a polarization direction in said sample on the basis of the difference between said polarization directions of said incident light and said transmitted light, said method further comprising the steps of:

changing and modulating said polarization direction "X" of said incident light;

detecting only a polarized component in a specific direction out of said light transmitted through said sample by a photosensor to obtain an output signal;

performing a phase sensitive detection on said output signal by using a signal for said modulating as a reference signal to obtain a demodulation signal "Y";

calculating an angle of rotation from 3 or more measuring points "Pi" (Xi, Yi) obtained from 3 or more polarization signals "Xi", where i denotes an integer of from 1 to n, where n denotes 3 or more, discretely selected from said polarization direction "X", and 3 or more demodulation signals "Yi", where i denotes an integer of from 1 to n and n denotes 3 or more, respectively corresponding to said polarization signals Xi; and measuring repeatedly at least one measuring point "Pi" out of said 3 or more measuring points "Pi" (Xi, Yi) when said calculated angle of rotation is judged not effective, to calculate again said angle of rotation on the basis of said measuring point "Pi" (Xi, Yi) measured repeatedly, and repeating said measurement until said angle of rotation is judged effective.

2. The method of polarimetry in accordance with claim 1, wherein when the number of said repeated measurement exceeds a prescribed number, said measurement action is stopped to stop said polarimetry for said sample.

3. The method of polarimetry in accordance with claim 1, wherein at least one measuring point "Pj" (Xj, Yj), where Xj≠Xi, other than said 3 or more measuring points "Pi" (Xi, Yi) is measured in said repeated measurement.

4. The method of polarimetry in accordance with claim 1, wherein said polarization direction "X" of said incident light is discretely changed into 3 or more polarization signals "Xi".

5. The method of polarimetry in accordance with claim 1, wherein said 3 or more measuring points "Pi" (Xi, Yi) are subjected to a linear regression treatment by using said "Xi" as criterion variables and said "Yi" as dependent variables on the basis of the principle of a least squares method to calculate a regression line represented by the equation (1):

$$Y=A+B\times X \quad (1)$$

where "Y" denotes a variable indicating said demodulation signal, "A" denotes a constant calculated, "B" denotes another constant calculated, and "X" denotes a variable indicating said polarization direction, and "X" is calculated from "A", "B" and a prescribed "Y" of said regression line to calculate said angle of rotation attributed to said sample on the basis of said "X".

6. The method of polarimetry in accordance with claim 5, wherein said calculated angle of rotation is judged effective when said "B" is not less than a prescribed minimum value or not more than a prescribed maximum value.

7. The method of polarimetry in accordance with claim 6, wherein said prescribed maximum value of said "B" is one calculated when a sample having a maximum transmittance is measured out of samples to be measured.

8. The method of polarimetry in accordance with claim 6, wherein the reliability of said calculated angle of rotation is evaluated on the basis of the fit between said measuring points "Pi" and said regression line.

9. A method of polarimetry by applying a magnetic field to a sample containing a spontaneously optical active substance and a magneto-optical active substance, allowing a light with a known polarization direction "X" to be incident upon said sample, changing and modulating a polarization direction of a light transmitted through said sample, and calculating an angle of rotation attributed to said sample on the basis of a magnitude of said magnetic field when an amount of change in an angle of rotation attributed to said spontaneously optical active substance and an amount of change in an angle of rotation attributed to said magnetic field satisfy a prescribed relation, said method comprising the steps of:

changing and modulating said polarization direction "X" of said incident light by applying said magnetic field;

detecting only a polarized component in a specific direction out of said light transmitted through said sample by a photosensor to obtain an output signal;

performing a phase sensitive detection on said output signal by using a signal for said modulating as a reference signal to obtain a demodulation signal "Y";

calculating an angle of rotation from 3 or more measuring points "Pi" (Xi, Yi) obtained from said magnetic field strengths "Xi", where i denotes an integer of from 1 to n and n denotes 3 or more, corresponding to 3 or more polarization signals discretely selected from said polarization direction "X", and 3 or more demodulation signals "Yi", where i denotes an integer of from 1 to n and n denotes 3 or more, respectively corresponding to said magnetic field strengths "Xi"; and measuring repeatedly at least one measuring point "Pi" out of said 3 or more measuring points "Pi" (Xi, Yi) when said calculated angle of rotation is judged not effective, to calculate again said angle of rotation on the basis of said measuring point "Pi" (Xi, Yi) measured repeatedly, and repeating said measurement until said angle of rotation is judged effective.

10. The method of polarimetry in accordance with claim 9, wherein when the number of said repeated measurement exceeds a prescribed number, said measurement action is stopped to stop said polarimetry for said sample.

11. The method of polarimetry in accordance with claim 9, wherein at least one measuring point "Pj" (Xj, Yj), where Xj≠Xi, other than said 3 or more measuring points "Pi" (Xi, Yi) is measured in said repeated measurement.

12. The method of polarimetry in accordance with claim 9, wherein said magnetic field strength is discretely changed into 3 or more magnetic field strengths.

13. The method of polarimetry in accordance with claim 9, wherein said 3 or more measuring points "Pi" (Xi, Yi) are subjected to a linear regression treatment by using said "Xi" as criterion variables and said "Yi" as dependent variables on the basis of the principle of a least squares method to calculate a regression line represented by the equation (1):

$$Y=A+B\times X \quad (1)$$

where "Y" denotes a variable indicating said demodulation signal, "A" denotes a constant calculated, "B" denotes another constant calculated, and "X" denotes a variable indicating said polarization direction, and "X" is calculated from "A", "B" and a prescribed "Y" of said regression line to calculate said angle of rotation attributed to said sample on the basis of said "X".

14. The method of polarimetry in accordance with claim 13, wherein said calculated angle of rotation is judged effective when said "B" is not less than a prescribed minimum value or not more than a prescribed maximum value.

15. The method of polarimetry in accordance with claim 14, wherein said prescribed maximum value of said "B" is one calculated when a sample having a maximum transmittance is measured out of samples to be measured.

16. The method of polarimetry in accordance with claim 14, wherein the reliability of said calculated angle of rotation is evaluated on the basis of the fit between said measuring points "Pi" and said regression line.

17. A method of polarimetry by allowing a light with a known polarization direction "X" to be incident upon a sample, detecting a polarization direction of a light transmitted through said sample, and measuring an angle of rotation of a polarization direction in said sample on the basis of the difference between said polarization directions of said incident light and said transmitted light, said method comprising the steps of:

changing and modulating said polarization direction "X" of said incident light;

detecting only a polarized component in a specific direction out of said light transmitted through said sample by a photosensor to obtain an output signal; performing a phase sensitive detection on said output signal by using a signal for said modulating as a reference signal to obtain a demodulation signal "Y"; and calculating an angle of rotation from two measuring points "Pi" (Xi, Yi) obtained from two polarization signals "Xi", where i denotes 1 and 2, discretely selected from said polarization direction "X", and two demodulation signals "Yi", where i denotes 1 and 2, respectively corresponding to said polarization signals Xi.

18. The method of polarimetry in accordance with claim 17, wherein at least one measuring point "Pi" out of said two measuring points "Pi" (Xi, Yi) is measured repeatedly when said calculated angle of rotation is judged not effective, to calculate again said angle of rotation on the basis of said measuring point "Pi" (Xi, Yi) measured repeatedly, and said measurement is repeated until said angle of rotation is judged effective.

19. The method of polarimetry in accordance with claim 18, wherein when the number of said repeated measurement exceeds a prescribed number, said measurement action is stopped to stop said polarimetry for said sample.

20. The method of polarimetry in accordance with claim 18, wherein at least one measuring point "Pj" (Xj, Yj), where Xj≠Xi, other than said two measuring points "Pi" (Xi, Yi) is measured in said repeated measurement.

21. The method of polarimetry in accordance with claim 17, wherein said polarization direction "X" of said incident light is discretely changed into two polarization signals "Xi".

22. The method of polarimetry in accordance with claim 17, wherein a line connecting said two measuring points "P1" (X1, Y1) and "P2" (X2, Y2) is calculated on the basis of the equation (5):

$$Y = E + F \times X \tag{5}$$

where "Y" denotes a variable indicating said demodulation signal, "E" denotes a constant calculated, "F" denotes another constant calculated and "X" denotes a variable indicating said polarization direction, "X" is calculated from "E", "F" and a prescribed "Y" of said line to calculate said angle of rotation attributed to said sample on the basis of said "X".

23. The method of polarimetry in accordance with claim 22, wherein said calculated angle of rotation is judged effective when said "F" is not less than a prescribed minimum value or not more than a prescribed maximum value.

24. The method of polarimetry in accordance with claim 23, wherein said prescribed maximum value of said "F" is one calculated when a sample having a maximum transmittance is measured out of samples to be measured.

25. A method of polarimetry by applying a magnetic field to a sample containing a spontaneously optical active substance and a magneto-optical active substance, allowing a light with a known polarization direction "X" to be incident upon said sample, changing and modulating s polarization direction of a light transmitted through said sample, and calculating an angle of rotation attributed to said sample on the basis of a magnitude of said magnetic field when an amount of change in an angle of rotation attributed to said spontaneously optical active substance and an amount of change in an angle of rotation attributed to said magnetic field satisfy a prescribed relation, said method comprising the steps of:

changing and modulating said polarization direction "X" of said incident light by applying said magnetic field;

detecting only a polarized component in a specific direction out of said light transmitted through said sample by a photosensor to obtain an output signal;

performing a phase sensitive detection on said output signal by using a signal for said modulating as a reference signal to obtain a demodulation signal "Y"; and calculating an angle of rotation from two measuring points "Pi" (Xi, Yi) obtained from said magnetic field strengths "Xi", where i denotes 1 and 2, corresponding to two polarization signals discretely selected from said polarization direction "X", and two demodulation signals "Yi", where i denotes 1 and 2, respectively corresponding to said magnetic field strengths "Xi".

26. The method of polarimetry in accordance with claim 25, wherein at least one measuring point "Pi" out of said two measuring points "Pi" (Xi, Yi) is measured repeatedly when said calculated angle of rotation is judged not effective, to calculate again said angle of rotation on the basis of said measuring point "Pi" (Xi, Yi) measured repeatedly, and said measurement is repeated until said angle of rotation is judged effective.

27. The method of polarimetry in accordance with claim 26, wherein when the number of said repeated measurement exceeds a prescribed number, said measurement action is stopped to stop said polarimetry for said sample.

28. The method of polarimetry in accordance with claim 26, wherein at least one measuring point "Pj" (Xj, Yj), where Xj≠Xi, other than said two measuring points "Pi" (Xi, Yi) is measured in said repeated measurement.

29. The method of polarimetry in accordance with claim 25, wherein said magnetic field strength is discretely changed into two magnetic field strengths.

30. The method of polarimetry in accordance with claim 25, wherein a line connecting said two measuring points "P1" (X1, Y1) and "P2" (X2, Y2) is calculated on the basis of the equation (5):

$$Y = E + F \times X \tag{5}$$

where "Y" denotes a variable indicating said demodulation signal, "E" denotes a constant calculated, "F" denotes another constant calculated and "X" denotes a variable indicating the polarization direction), and "X" is calculated from "E", "F" and a prescribed "Y" of said line to calculate said angle of rotation attributed to said sample on the basis of said "X".

31. The method of polarimetry accordance with claim 30, wherein said calculated angle of rotation is judged effective when said "F" is not less than a prescribed minimum value or not more than a prescribed maximum value.

32. The method of polarimetry in accordance with claim 31, wherein said prescribed maximum value of said "F" is one calculated when a sample having a maximum transmittance is measured out of samples to be measured.

* * * * *